United States Patent [19]

Kebabian

[11] Patent Number: 5,760,895
[45] Date of Patent: Jun. 2, 1998

[54] OPTICAL MONITOR FOR WATER VAPOR CONCENTRATION

[75] Inventor: Paul Kebabian, Acton, Mass.

[73] Assignee: Aerodyne Research, Inc., Billerica, Mass.

[21] Appl. No.: 700,026

[22] Filed: Aug. 20, 1996

[51] Int. Cl.$^6$ .................... G01N 21/31; G01N 21/35
[52] U.S. Cl. .................... 356/307; 250/339.13; 250/345
[58] Field of Search .................... 356/73, 349, 350, 356/351, 346, 301, 303, 319, 322, 327, 316, 307, 311, 312, 315, 436, 437; 372/28, 29, 37, 32, 20, 22, 26; 250/339, 343, 344, 345, 339.13

[56] References Cited

U.S. PATENT DOCUMENTS

| | | | |
|---|---|---|---|
| 4,035,083 | 7/1977 | Woodriff et al. | 356/115 |
| 4,341,470 | 7/1982 | Parker et al. | 356/307 |
| 4,397,025 | 8/1983 | Kebabian | 372/37 |
| 4,595,292 | 6/1986 | Amodeo et al. | 356/346 |
| 4,718,763 | 1/1988 | Oishi et al. | 356/326 |
| 4,849,637 | 7/1989 | Cerff et al. | 250/345 |
| 4,926,429 | 5/1990 | Chung | 372/32 |
| 5,026,991 | 6/1991 | Goldstein et al. | 250/343 |
| 5,181,077 | 1/1993 | Dencks et al. | 356/307 |
| 5,650,845 | 7/1997 | Kebabian | 356/307 |

*Primary Examiner*—Frank G. Font
*Assistant Examiner*—Michael P. Stafira
*Attorney, Agent, or Firm*—Cesari and McKenna, LLP

[57] ABSTRACT

A system for measuring and monitoring water vapor concentration in a sample uses as a light source an argon discharge lamp, which inherently emits light with a spectral line that is close to a water vapor absorption line. In a preferred embodiment, the argon line is split by a magnetic field parallel to the direction of light propagation from the lamp into sets of components of downshifted and upshifted frequencies of approximately 1575 Gauss. The downshifted components are centered on a water vapor absorption line and are thus readily absorbed by water vapor in the sample; the upshifted components are moved away from that absorption line and are minimally absorbed. A polarization modulator alternately selects the upshifted components or downshifted components and passes the selected components to the sample. After transmission through the sample, the transmitted intensity of a component of the argon line varies as a result of absorption by the water vapor. The system then determines the concentration of water vapor in the sample based on differences in the transmitted intensity between the two sets of components. In alternative embodiments alternate selection of sets of components is achieved by selectively reversing the polarity of the magnetic field or by selectively supplying the magnetic field to the emitting plasma.

18 Claims, 4 Drawing Sheets

OPTICAL MONITOR FOR WATER VAPOR CONCENTRATION

This invention was made with government support under Department of Energy Contract No. DE-FG02-93ER81915.A000. The government has certain rights in this invention.

FIELD OF THE INVENTION

This invention relates generally to optical sensors and, more particularly, to sensors for measuring the concentration of water vapor in a sample.

BACKGROUND OF THE INVENTION

Sensors for measuring water vapor concentration in a gaseous sample are employed in a wide variety of endeavors, ranging from meteorological research to process control in paper production. Prior-art water vapor sensors have been based on diverse physical principles, including the condensation of the vapor from the sample onto a cold surface; and the physical or chemical interaction of water vapor in the sample with another medium, followed by detection of the resulting change in some property, such as dielectric constant or electrical conductivity, of the medium. Such sensors require frequent calibration and suffer from defects such as slow response time, limited detectable moisture range and limited utility for samples distributed over an extended volume. Also, these techniques require contact between the sample and some potentially contaminating foreign body and alter, at least temporarily, the water vapor concentration in the sample being measured.

In a less invasive approach to water vapor measurement, the sample is exposed to ultraviolet light, which the water vapor absorbs; the detected fluorescence of the resulting decomposition products serves as a basis for calculating the water content of the sample. The apparatus required for this technique is complex, large, and costly to manufacture and operate.

Optical spectroscopic analysis techniques are generally applicable to samples distributed over an extended volume, operable without contact between the sample and a foreign body, and offer greater concentration range and sensitivity. Spectroscopic water vapor measurement is accomplished by observing the change in light having a wavelength that is relatively readily absorbed by water vapor, termed the analytical wavelength, resulting from transmission of the light through the sample to be analyzed. Moisture detection by infrared spectroscopy usually employs either a conventional instrument such as a Fourier transform spectrometer, a large, heavy, highly power-consumptive apparatus; or a costly and complex system including laser tuned to emit light at a wavelength coincident with a line in the water vapor absorption spectrum. In particular, systems including diode lasers require a skilled and attentive operator, or a complicated feedback mechanism, to maintain the desired emitted wavelength and intensity since the laser properties change unpredictably as the laser ages.

In addition to radiation at the analytical wavelength, readily absorbed by water vapor in the sample, spectroscopic techniques generally require reference radiation for distinguishing optical absorption by the water vapor from optical absorption by other entities, for example smoke or dust, in the pathway from the source of radiation through the sample. An ideal reference wavelength is minimally absorbed by water vapor, but other entities interact with it indistinguishably from their interaction with the analytical wavelength. In order to provide this similarity in behavior to the analytical radiation, the reference radiation is preferably as close as possible in wavelength to the analytical radiation without also being readily absorbed by water vapor.

Although alternate types of light sources, without the disadvantages of prior-art sources, exist, finding such a source that emits at a wavelength optimally overlapping a water vapor absorption line is not a straightforward matter. Finding such a source that also provides an appropriate reference wavelength is even more difficult.

SUMMARY OF THE INVENTION

The invention determines water vapor concentration in a sample based on absorption by the sample of light emitted by an argon discharge lamp. In particular, the invention uses a spectral line emitted by the neutral argon atom having a wavelength (in air) of approximately 935.4 nm. This line, designated 1s2-2p7 in Paschen notation, is close to one of water vapor's absorption lines, namely the line having upper level rotational quantum numbers (J, $K_{79}$, $K_C$) of (404) and lower level numbers of (303) in the $2\upsilon_1+\upsilon_3$ vibrational band; the exact wavelengths (in vacuo) are 935.679 nm and 935.685 nm for these argon and water vapor lines, respectively. Hereinafter, these lines are referred to as simply the argon line and the water vapor line.

For the purposes of this disclosure, a sample is any expanse of space in which water vapor concentration is to be determined. The sample may contain a relatively static body of gas confined, for example, by a glass enclosure. Or, the sample may be a specimen representing a less-well-defined region, such as a large room or a volume of the earth's atmosphere.

In its simplest configuration, the system evaluates the water vapor concentration in the sample based on the change in intensity at the argon line wavelength, relative to the line intensity emitted by the lamp, of light that has passed through the sample. In a preferred embodiment, a magnetic field parallel to the direction of the light propagation is applied to the lamp. In accordance with the well-known Zeeman effect, the magnetic field alters energy levels of the argon atoms in the plasma, which in turn alters the emitted wavelengths, effectively splitting the light into a set of downshifted-frequency components and a set of upshifted-frequency components having, respectively, longer and shorter wavelengths compared to the unsplit line emitted in the absence of the field. The components of each of these sets are uniformly circularly polarized such that one set has a polarization opposite to that of the other set. The magnitude of the wavelength shift and the relative amplitudes of the components within each set varies with the strength of the applied magnetic field. The Zeeman splitting has two beneficial effects. First, the downshifted components are closer to the water vapor line, and consequently more strongly absorbed, than is the unsplit line or the upshifted components. Second, the spectral proximity of the upshifted components or, alternatively, the unsplit line to the downshifted components provides a suitable reference wavelength. The invention applies various of the constituents of the argon line—the unsplit line and the Zeeman-split components—to the sample in a time-multiplexed fashion to enable precise moisture concentration determination.

The invention encompasses several approaches to this time-multiplexing. In one approach, light from the downshifted and upshifted components are alternately allowed into the sample. For example, the alternation may be achieved by time-variant filtering of the split argon line or by passing light emitted by the discharge under periodic polarity-reversal of the applied magnetic field through a circular polarizer of fixed handedness. The longer-wavelength, downshifted components are relatively strongly absorbed by water vapor in the sample; the intensity change at the downshifted frequencies observed after the light has traveled through the sample comprehends this absorption and other interactions along the pathway from the lamp through the sample. The shorter-wavelength upshifted components are only weakly absorbed by water vapor; the observed intensity change at the upshifted frequencies reflect the other interactions and is thus useful in reckoning the portion of the absorption at the downshifted frequencies truly due to water vapor. In another approach, the unsplit argon line and one or more of the Zeeman-split components are alternately allowed into the sample, for example by applying the magnetic field only alternately. In this case, the unsplit argon line serves as the reference wavelength. The upshifted Zeeman-split component is optionally excluded from the sample in order to enhance the contrast in absorption between the downshifted Zeeman-split component and the unsplit argon line.

In a preferred embodiment, upshifted and downshifted components are alternately selected for transmission into the sample on the basis of their respective polarizations. This approach provides analytical and reference wavelengths sufficiently far apart so that broadening of the water vapor absorption line due to a higher-than-atmospheric sample pressure does not cause an unacceptable reduction in the differential absorption between the reference and analytical wavelengths. A polarization modulator for performing this selection consists of three components in succession: (i) a quarter-wave plate that converts the circular polarizations of the upshifted and downshifted components to linear polarizations; (ii) a liquid-crystal cell that, according to whether or not it is energized, refrains from rotating or rotates by 90 degrees the linear polarizations of the upshifted and downshifted components; and (iii) a linear polarizer that passes components of a particular polarization and blocks components of the orthogonal polarization. After passing through the quarter-wave plate, the upshifted and downshifted components have mutually perpendicular linear polarizations upon entering the liquid-crystal cell. The cell is periodically energized and de-energized, such that the polarization of a each of the upshifted and downshifted components entering it is alternately converted between two mutually orthogonal states and alternately passed and blocked by the fixed linear polarizer. Thus, the weakly absorbed upshifted and strongly absorbed downshifted components of the light are alternately passed through the linear polarizer to the sample in which water vapor is to be measured, thereby defining two distinct modes of operation.

In an alternative embodiment, polarization modulation is achieved by alternately reversing the polarity of the magnetic field, thereby interchanging the circular polarizations of the upshifted and downshifted components, and passing the split argon line through a fixed circular polarizer which passes the component having a particular circular polarization and blocks the component having the opposite handedness. Accordingly, the field polarity reversal selects the component to be passed through the circular polarizer to the sample.

In another alternative embodiment, the downshifted components and the unsplit argon line are alternately selected by supplying and removing the magnetic field. When the magnetic field is applied, the argon line is split into the sets of upshifted and downshifted components, as discussed above. When these components are passed through the sample, the downshifted component is readily absorbed. When the magnetic field is absent, the argon line produced by the lamp is passed, unshifted, directly to the sample. Since the unsplit argon line has a wavelength that is close to but not coincident with that of the water vapor line, the water vapor does not absorb the unsplit line as readily. The differential absorption between the shifted components and the unshifted argon line are then used to determine the water vapor concentration.

In this alternative embodiment, a circular polarizer is optionally included for excluding the upshifted component from the sample. This embodiment, especially if used without the circular polarizer, is most appropriate for application to a sample at a pressure well below normal atmospheric pressure, under which condition the narrowing of the water vapor line enhances the difference between absorption of the downshifted component compared to absorption of the unsplit line. Inclusion of the circular polarizer introduces optical losses but is nevertheless advantageous for application to a sample in which the water line is broadened due to elevated pressure, in that excluding the upshifted components maximizes the contrast in absorption between field-on and field-off modes of operation.

In both modes, before the light enters the sample, it passes through an optical tap, which extracts a portion of the light and transmits it to a first detector, such as a photodiode. This detector produces a first output signal that is proportional to the intensity of the extracted light. The remainder of the light is transmitted through the sample and then enters a second detector, which produces a second output signal, proportional to the light intensity after interaction with the sample. The system then determines the concentration of water vapor in the sample from the output signals of the two photodiodes during the two modes of operation, i.e., the mode in which weakly absorbed components traverse the sample and the mode in which strongly absorbed components traverse the sample. The first output signal is preferably used to compensate for random fluctuations in the lamp output and for differential amplitude modulation by other system elements between the two modes of operation.

The properties of the present system make it especially well suited to measuring water vapor concentrations in the low parts-per-million range under conditions prevailing in the stratosphere. The sensor can potentially be built as a small, light-weight, low-power-consumption device suitable for atmospheric studies conducted from a small remotely piloted aircraft.

The elements making up the system are relatively inexpensive and robust. As an argon lamp ages, the internal operating conditions of the discharge plasma (chiefly, the pressure), gradually change, but the resulting changes in the emitted spectrum, such as the center wavelength and width of the line of interest, are small enough as to have no significant effect other than a gradual drop in the light output. Should the lamp need to be replaced, it costs only a few dollars. Other elements of the system are even less likely to require replacement.

Thus, in one or more of its embodiments, the invention provides an inexpensive, sensitive, sturdy water vapor sensor with a rapid response time and long operating life.

BRIEF DESCRIPTION OF THE DRAWINGS

The above and further advantages of the invention may be better understood by referring to the following description in conjunction with the accompanying drawings, in which.

DETAILED DESCRIPTION OF ILLUSTRATIVE EMBODIMENTS

Figure 1:
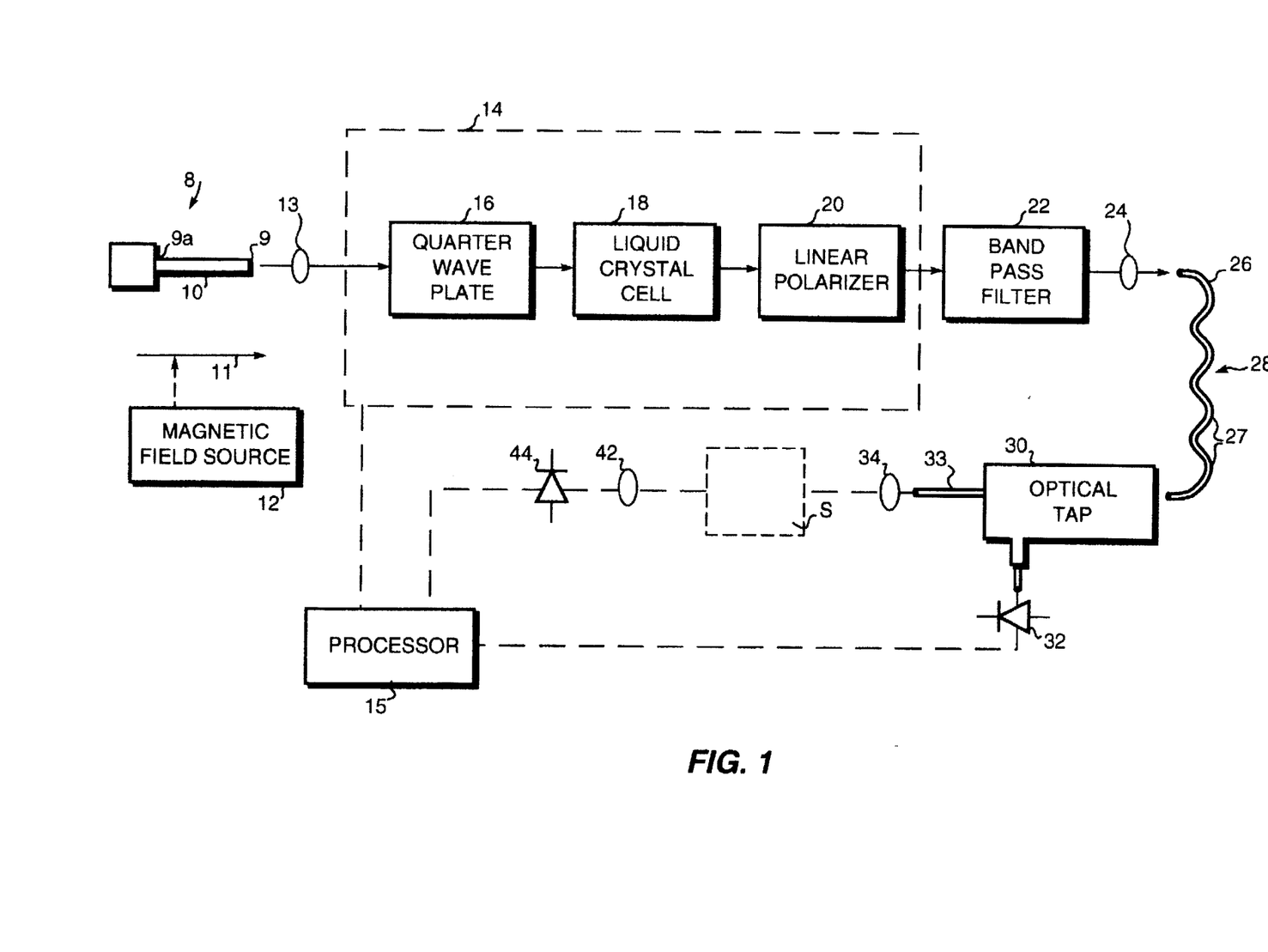
FIG. 1 is a functional block diagram of a system constructed in accordance with a preferred embodiment.

With reference to FIG. 1, a system for measuring water vapor concentration in a sample S according to the invention includes an argon discharge lamp 8 containing an argon plasma which emits light at a wavelength of approximately 935 nanometers. The lamp 8 is preferably of a design that, in conjunction with the arrangement of the other elements of the system, optimizes the spectral intensity that reaches the sample S from the relatively weak 935-nm line. A capillary-tube positive-column lamp similar to those used, for example, as ultraviolet sources for photoionization detectors is useful in this regard. (Of course, the present invention does not require an ultraviolet-transmissive window; ordinary glass is suitable in the 935-nm spectral region.) The light ultimately provided to the sample S leaves the lamp 8 through a window in the near end 9 of the capillary tube 10. The dimensions of the capillary tube 10 and other operating parameters of the lamp 8 are chosen to provide appropriate optical coupling to the other elements of the system, particularly to the optical fiber 26, described below.

A magnetic field source 12 applies to the emitting plasma a magnetic field oriented parallel to the direction of light propagation from the lamp 8, as indicated by arrow 11. The field splits the argon line into two sets of components, one at upshifted frequencies relative to the unsplit argon line and the other at downshifted frequencies having opposite circular polarizations relative to one another. The optimum coincidence between the set of downshifted components and the water vapor line has been found to occur under a field strength of approximately 1575 Gauss. Only minor variation in differential absorption by water vapor occurs for field strengths of approximately ±100 Gauss of this value.

Light from the lamp 8 passes through a series of elements before entering the sample S. A collimator lens 13 collimates the light, which is then processed by a polarization modulator 14. A processor 15 is coupled to the polarization modulator 14 so as to alternately select the upshifted and downshifted components from the light for transmission to the sample.

The polarization modulator 14 includes a quarter-wave plate 16, a liquid-crystal cell 18 and a linear polarizer 20. The quarter-wave plate 16 converts the opposite circular polarizations of the components in the collimated light to orthogonal linear polarizations. The linearly polarized components then enter the liquid crystal cell 18, which is in either an energized state or a de-energized state. When the cell 18 is in the de-energized state, it rotates the linearly polarized components by 90 degrees, and thus, interchanges the polarizations of the sets of components. When the cell is in its energized state, it does not alter the polarizations. The linear polarizer 20 receives the components transmitted by the cell 18 and, according to its configuration, passes the set of components having a particular linear polarization, and blocks the set with the orthogonal polarization. Thus, it passes only one of the sets of shifted components processed by the liquid-crystal cell 18 in the de-energized state and passes only the other set of shifted components processed by the cell 18 in the energized state. As a result, the linear polarizer 20 alternately passes the set of components that is readily absorbed by water vapor and the set of components that is minimally absorbed.

A bandpass filter 22 is included to filter extraneous components, particularly the other spectral lines emitted by the argon lamp 18, from the polarization-modulated light. Suitable bandpass filters are widely available, typically being made of multiple layers of dielectric films as is well known to those skilled in the art. The system is configured so that the collimator lens 13 images the far end 9 of the end of the capillary tube 10 onto an aperture 23. A reimaging lens 24 focuses the light passing through the aperture 23 into an optical fiber 26.

Figure 2:
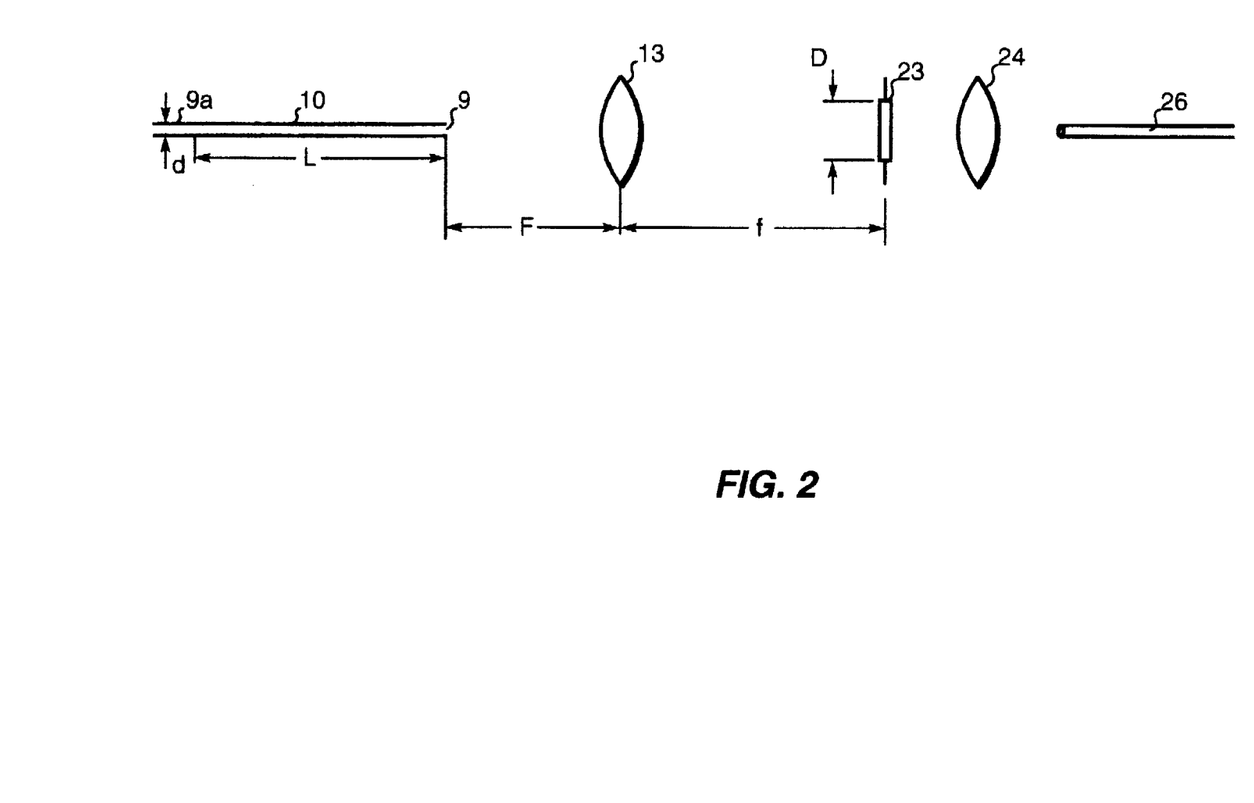
FIG. 2 shows the relative placement of focusing elements in the system.

The relative placements and properties of the lamp 8, the collimator lens 13, the aperture 23, and the reimaging lens 24 are critical to the operation of the system. In FIG. 2 these elements are shown without the intervening polarization modulator 14 and bandpass filter 22. The near end 9 of a capillary tube 10 having length L and diameter d is separated from the collimator lens 13 by the focal length F of the lens 13, so that the far end 9a of the tube 10 is situated L+F away from the lens 13. The aperture 23 is displaced from the lens 13 by a distance f such that the far end 9a is imaged onto the plane of the aperture 23. If the aperture 23 has diameter D equal to $$\frac{df}{(L+F)},$$

any ray of light that leaves the capillary tube 10 after being reflected from the inner wall of the tube 10 will be excluded by the aperture 23 from entering the optical fiber 26. This feature is essential for embodiments employing polarization modulation because reflection by the wall of the tube 10 depolarizes the light.

It is further desirable that the arrangement of these elements maximize the light intensity delivered to the fiber 26 so that the throughput, i.e., the product of the cross sectional area and the solid angle of the beam that it accepts, of the fiber 26 is fully exploited. For a fiber of diameter $d_f$, an arrangement conforming to $$L = \frac{d^2}{2d_f N},$$

in which N is equal to the sine of the half-angle of the cone of rays accepted by the fiber, will fill the fiber to capacity. A fiber 26 having $d_f$=200 μm and N=0.4 has been found to be suitable for receiving the output of a 1-mm-diameter lamp having argon pressure of about 7 Torr and lamp current of about 5 mA.

The focal length of the reimaging lens 24 is selected to match the angular spread of the light passed by the aperture 23 to the diameter $d_f$ of the fiber 26. The aperture 23 and the end of the fiber 26 are at the back and front focal planes, respectively, of the reimaging lens 24.

Inside the fiber 26, the angles of the individual light rays are randomized with respect to the axis of the fiber 26 in strategically placed bends 27 which collectively serve as a mode scrambler 28. The scrambler 28, which is a familiar component in the fiber optics art, renders the light more uniform with respect to the intensity distribution across the fiber cross section and the range of directions of propagation inside the fiber 26. This uniformity enables an optical tap 30 to direct a constant fraction, regardless of small fluctuations in the angular or spatial distribution of the light emitted by the lamp 8 of the light coupled to the fiber 26 to a first photodiode 32. In response, the first photodiode 32 produces a signal $D_1$ proportional to the intensity of the beam entering the sample S.

The optical tap 30 passes the remainder of the light to a fiber 33, which conveys the light to a first focusing lens 34 positioned to direct it into the sample S. A second focusing lens 42 directs light leaving the sample S to a second photodiode 44, which produces a signal $D_2$ proportional to that light, so that the ratio of the first and second photodiode signals $D_2/D_1$ indicates the transmission of the optical path, including both the effect of absorption by water vapor and of absorption by other materials in the optical path.

The processor 15 is coupled to the photodiodes 32, 44 and to the polarization modulator 14 and synchronizes processing of the photodiode signals $D_1$ and $D_2$ with the operation of the polarization modulator 14 to distinguish signals produced during the two modes of operation, i.e., the mode in which the modulator 14 passes weakly absorbed components to the sample and the mode in which the modulator 14 passes readily absorbed components. Based on the disparity in the absorption indicated by the signals produced in the two modes, the processor 15 determines the water vapor concentration in the sample S. Preferably, the signal $D_1$ produced during transmission of the weakly-absorbed upshifted components to the sample S is adjusted by a scaling factor $\alpha$ so that the difference signal $\alpha D_1 - D_2$ is zero. During transmission of the readily-absorbed downshifted components, the same value of $\alpha$ is used. Thus, the signal $\alpha D_1 - D_2$, normalized by $D_1$, produced during transmission of the downshifted components is proportional to the absorption by water vapor, and is independent of absorption by other materials in the optical path.

Note that this difference signal is much less sensitive to fluctuations in lamp output than is either signal $D_1$ or $D_2$ alone. It is also relatively insensitive to spurious modulation of the light intensity due to effects such unequal transmission through the liquid crystal cell 18 in its two states. Thus, potential sources of noise and drift, respectively, are eliminated from the water vapor measurement. When the processor 15 adjusts $D_1$ in this manner and subtracts $D_2$ therefrom, it is functioning as an electrically balanced bridge, similar to a transmission bridge used, for example, for measuring the properties of microwave components.

The processor 15 may incorporate analog electronic elements, such as lock-in amplifiers, that process the signals $D_1$, and $D_2$ as received from the photodiodes 32, 44 or include a mechanism for converting the signals to digital form and a digital microprocessor for executing the computations. However, it is often advantageous to perform the scaling and subtraction in the analog domain, since this approach minimizes the dynamic range required for the subsequent signal processing (such as establishing the appropriate value of $\alpha$) if there are significant fluctuations in the lamp output or other sources of noise that are to be reduced by the scaling and subtraction. Also instead of the computing the water vapor concentration itself, the system may be used to determine whether or not the concentration exceeds or falls below a predetermined level. In this case, the processor determines, for example, whether the signal produced by the bridge circuit in response to the upshifted components being passed through the sample is greater or less than a predetermined threshold value.

Figure 3A:
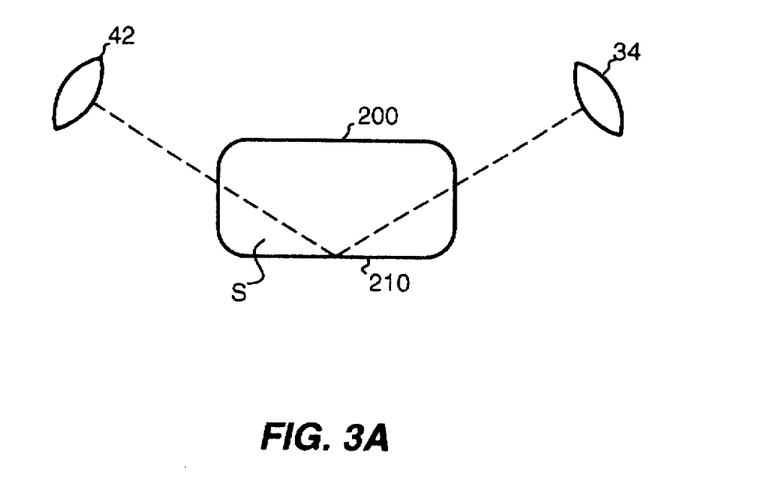
FIGS. 3A and 3B illustrate two alternative path configurations through the sample.
Figure 3B:
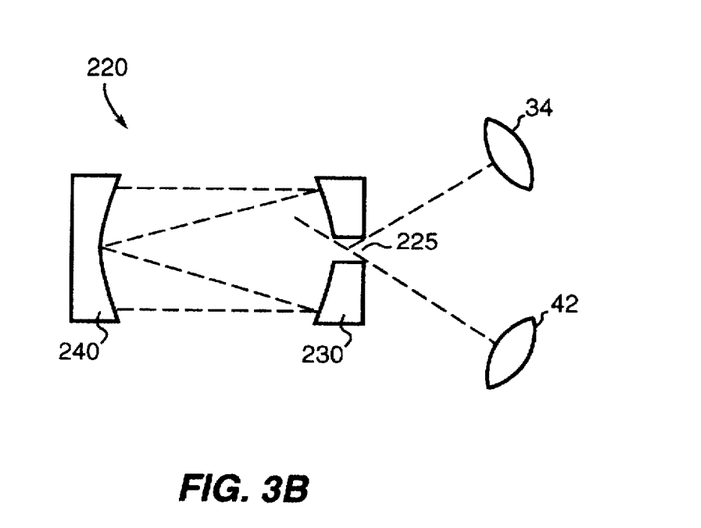
Figure 4:
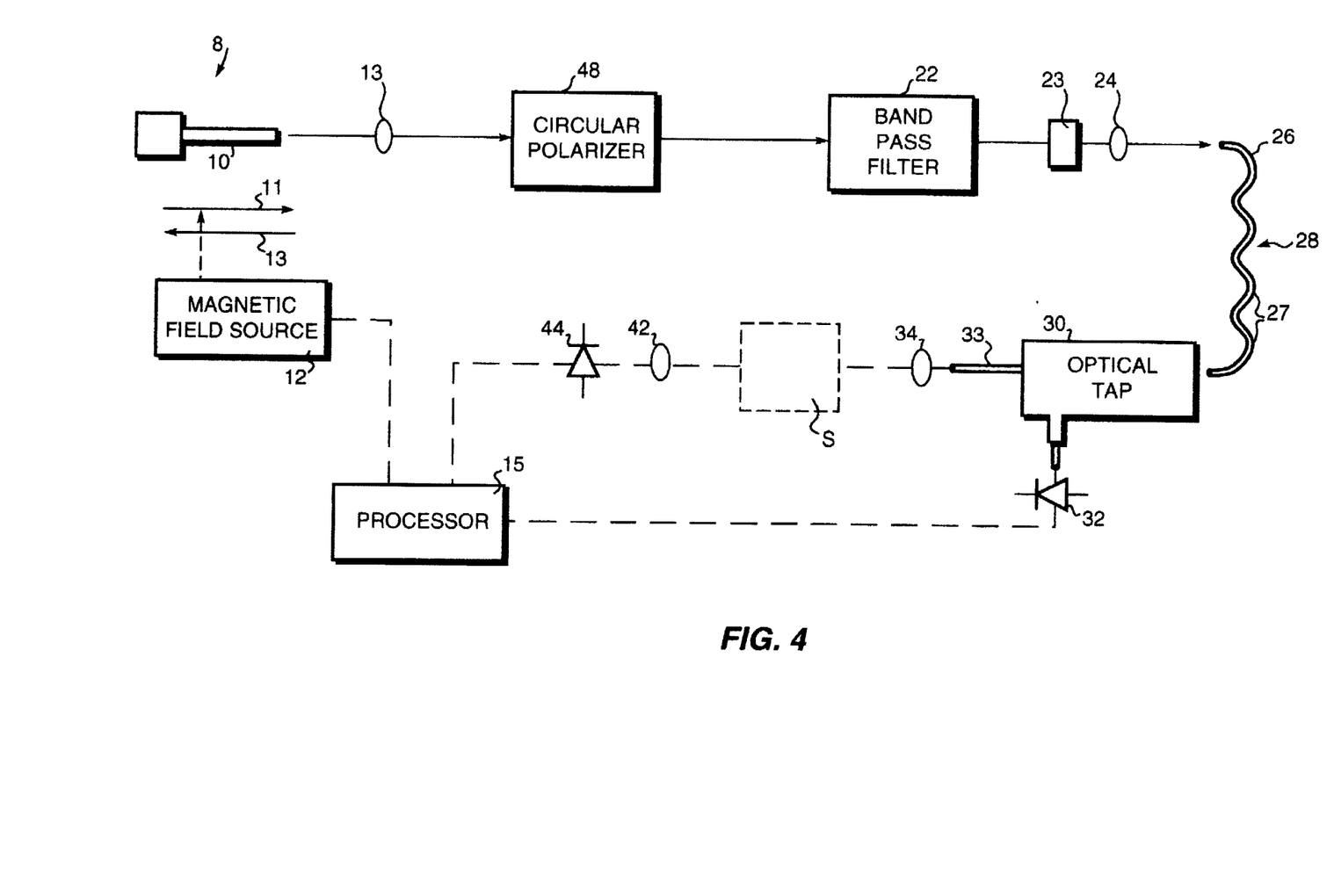
FIG. 4 is a functional block diagram of a system constructed in accordance with an alternative embodiment.

The configuration of system elements may be adjusted to augment the path length of the light through the sample S in order to obtain larger absorption signals and thus better concentration resolution compared to those obtained using the direct single-pass arrangement shown in FIG. 1. For example, light entering the sealed glass cell 200 shown in FIG. 3A is reflected by a surface 210 before exiting the sample S and entering the second refocusing lens 42. A multiple-pass absorption cell 220, shown in FIG. 3B, is useful when the sample is not confined to a sealed cell but is in an open region, such as a room or the earth's atmosphere. In this structure, the first focusing lens 34 couples light into the cell 220 through a hole 225 in a mirror 230. The mirror 230 and an opposing mirror 240 reflect the light between them several times. In the last pass, the mirror 240 directs the light from the cell 220 through the hole 225 to the second focusing lens 42. A specimen of gas from the region may be allowed to diffuse into the multiple-pass cell 220 or the specimen may be drawn into the cell 220 by a small pump or fan (not shown).

With reference to FIG. 3, in an alternate embodiment, readily absorbed downshifted and weakly absorbed upshifted components are alternately selected by a fixed circular polarizer 48 in conjunction with reversal of the polarity of the magnetic field produced by the magnetic field source 12, rather than by the polarization modulator 14 shown in FIG. 1. Under the control of the processor 15, the magnetic field source 12 alternately supplies a magnetic field that is oriented parallel and antiparallel to the direction of light propagation from the lamp 8, as indicated, respectively, by arrows 11 and 13. The change in the polarity of the magnetic field interchanges the circular polarizations of the upshifted and downshifted components. According to the polarity of the field, the fixed circular polarizer 48 passes one of these sets of components to the optical fiber 26 and blocks the other set. The processor 15 synchronizes processing of the photodiode signals with operation of the magnetic field source 12 to distinguish signals produced during the two modes of operation.

In another alternative embodiment, the magnetic field source 12 of FIG. 3 is configured to alternately turn on and off, thereby alternately providing to the sample S the readily absorbed downshifted components and the less-readily absorbed unsplit light. The fixed circular polarizer 48 is thus no longer required for selection of the analytical and reference wavelengths. However, the polarizer 48 is desirable for excluding the upshifted components from the sample, thereby enhancing the contrast in differential absorption between the two modes of operation. If the system does not use polarization to select analytical or reference components, the aperture 23 is not necessary.

The foregoing description has been limited to specific embodiments of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A system for determining a concentration of water vapor in a sample, the system comprising:
   a. an argon discharge lamp for supplying $1S_2$-$2P_7$ spectral line light, having a wavelength of approximately 935 nm, to the sample; and
   b. means for evaluating the concentration of water vapor in the sample based on a change in intensity of the light supplied by the lamp to the sample.

2. The system of claim 1 further comprising:
   a. a magnetic field source for applying a magnetic field to the lamp, the magnetic field splitting the spectral line supplied by the lamp into downshifted components having longer wavelengths that are readily absorbed by water vapor and upshifted components having shorter wavelengths that are less-readily absorbed by water vapor; and b. selection means for selectively passing the downshifted components to the sample;

the means for evaluating the concentration of water vapor in the sample evaluating the concentration based on a change in intensity of the downshifted components passed to the sample.

3. The system of claim 2 wherein the means for evaluating the concentration of water vapor comprises:

a. a first detector for producing a first signal which is proportional to the intensity of the downshifted components before the downshifted components have passed through the sample;

b. a second detector for producing a second signal which is proportional to the intensity of the downshifted components after the downshifted components have passed through the sample; and c. means for computing, from the ratio of the first signal to the second signal, the concentration of water vapor in the sample.

4. The system of claim 3 wherein the selection means selectively passes to the sample the upshifted components or the downshifted components, the first detector produces a first reference signal which is proportional to the intensity of the upshifted components before the upshifted components have passed through the sample and the second detector produces a second reference signal which is proportional to the intensity of the upshifted components after the upshifted components have passed through the sample, the means for computing determining, based on a difference between the first and second reference signals associated with the set of upshifted components, a correction to be included in computing the concentration of water vapor based on the first and second signals associated with the set of downshifted components.

5. The system of claim 4 wherein the first and second detectors are first and second photodiodes, the means for computing the concentration of water vapor comprises a bridge including the photodiodes, electrically balanced when the set of upshifted components are passed to the sample, and the means for computing produces a concentration signal that is proportional to the concentration of water vapor in the sample when the set of downshifted components are passed to the sample.

6. The system of claim 5 wherein the means for computing the concentration of water vapor determines whether the concentration exceeds or falls below a predetermined level by determining whether the concentration signal produced by the bridge exceeds or falls below a predetermined value.

7. The system of claim 2 wherein the means for evaluating the concentration of water vapor determines whether the concentration exceeds or falls below a predetermined level.

8. The system of claim 2 wherein the downshifted components have a downshifted circular polarization and the upshifted components have an upshifted circular polarization opposite to the downshifted circular polarization, the selection means selectively passing to the sample the downshifted components or the upshifted components based on their respective circular polarizations.

9. The system of claim 8 wherein the selection means comprises:

a. means for linearizing the respective circular polarizations of the downshifted and upshifted components thereby converting the downshifted circular polarization to a downshifted linear polarization and the upshifted circular polarization to an upshifted linear polarization, orthogonal to the downshifted linear polarization;

b. rotating means for selectively rotating the linearly polarized downshifted and upshifted components by 90 degrees, the rotating means alternately operating in a first mode, in which it refrains from rotating the components and in a second mode, in which it rotates each of the components such that each component has a linear polarization orthogonal to the respective linear polarization it has without rotation; and c. a linear polarizer for passing components having a particular linear polarization and blocking components that do not have the particular polarization thereby passing upshifted components while blocking downshifted components and passing downshifted components while blocking upshifted components.

10. The system of claim 2 wherein the downshifted components have a downshifted circular polarization and the upshifted components have an upshifted circular polarization, the selection means selectively passing to the sample the downshifted components or the upshifted components, the selection means comprising:

a. means for controlling the magnetic field source, such that the magnetic field source selectively reverses the polarity of the magnetic field, thereby interchanging the upshifted circular polarization and the downshifted circular polarization; and b. a circular polarizer, for passing components having a particular circular polarization and blocking components that do not have the particular circular polarization, thereby passing upshifted components while clocking downshifted components and passing downshifted components while clocking upshifted components.

11. The system of claim 2 wherein the selection means comprises means for alternately turning on and off the magnetic field source, such that the light produced by the lamp is alternately (i) split into the sets of upshifted and downshifted components and (ii) not split into the sets of components, the selection means alternately passing to the environment of interest split components and the unsplit light.

12. The system of claim 11 further comprising means for blocking the upshifted components from entering the sample.

13. The system of claim 2 wherein the magnetic field has a strength of approximately 1575 Gauss.

14. The system of claim 3 wherein the selection means selectively passes to the sample unsplit light or downshifted components, the first detector produces a first reference signal which is proportional to the intensity of the unsplit light before the unsplit light has passed through the sample and the second detector produces a second reference signal which is proportional to the intensity of the unsplit light after the unsplit light has passed through the sample, the means for computing determining, based on a difference between the first and second reference signals associated with the unsplit light, a correction to be included in computing the concentration of water vapor based on the first and second signals associated with the set of downshifted components.

15. The system of claim 14 wherein the first and second detectors are first and second photodiodes, the means for computing the concentration of water vapor comprises a bridge including the photodiodes, electrically balanced when the unsplit light is passed to the sample, and the means for computing produces a concentration signal that is proportional to the concentration of water vapor in the sample when the set of downshifted components are passed to the sample.

16. A system for determining a concentration of water vapor in a sample, the system comprising:

a. an argon discharge lamp for supplying light of the $1S_2$-$2P_7$ spectral line, having a wavelength in the vicinity of 935 nm, to the sample; and b. a magnetic field source for applying a magnetic field to the lamp, the field splitting the spectral line supplied by the lamp into downshifted components having longer wavelengths that are readily absorbed by water vapor and upshifted components having shorter wavelengths that are less readily absorbed by water vapor, the downshifted components having a first circular polarization and the upshifted components having a second circular polarization, opposite to the first circular polarization;

c. control means for selectively controlling the magnetic field source so as to selectively apply a magnetic field having a polarity equal to one value or to an opposite value, the polarity determining the respective circular polarizations of the sets of upshifted and downshifted components;

d. a circular polarizer for selectively passing to the sample set of upshifted components or the set the downshifted components, depending on the orientations of the respective circular polarizations; and e. means for determining the concentration of water vapor in the sample based on a change in intensity of the light including the set of downshifted components supplied to the sample.

17. A system for determining a concentration of water vapor in a sample, the system comprising:

a. an argon discharge lamp for supplying $1 S_2$-$2P_7$ spectral line light, having a wavelength approximately 935 nm, to the sample;

b. a magnetic field source for applying a magnetic field to the lamp, the field splitting the spectral line supplied by the lamp into downshifted components having longer wavelengths that are readily absorbed by water vapor and upshifted components having shorter wavelengths that are less-readily absorbed by water vapor;

c. control means for selectively turning on and off the magnetic field source; and d. means for determining the concentration of water vapor in the sample based on (i) a change in intensity of light being supplied to the sample while the magnetic field source is turned on, and (ii) a change in intensity of light supplied to the sample while the magnetic field source is turned off.

18. A system for determining a concentration of water vapor in a sample, the system comprising:

a. an argon discharge lamp for supplying $1S_2$-$2P_7$ spectral line light, having a wavelength of approximately 935 nm, to the sample; and b. a magnetic field source for applying a magnetic field to the lamp, the field splitting the spectral line supplied by the lamp into downshifted components having longer wavelengths that are readily absorbed by water vapor and upshifted components having shorter wavelengths that are less readily absorbed by water vapor, the downshifted components having a first circular polarization and the upshifted components having a second circular polarization, opposite to the first circular polarization;

c. a polarization modulator for selectively passing upshifted and downshifted components to the sample, the polarization modulator comprising i. a quarter-wave plate for linearizing the respective circular polarizations of the downshifted and upshifted components thereby converting the downshifted circular polarization to a downshifted linear polarization and the upshifted circular polarization to an upshifted linear polarization, orthogonal to the downshifted linear polarization;

ii. a liquid-crystal cell for selectively rotating the linearly polarized downshifted and upshifted components by 90 degrees, the cell alternately operating in a first mode, in which it refrains from rotating the components and in a second mode, in which it rotates each of the components such that each component has a linear polarization orthogonal to the respective linear polarization it has without rotation;

iii. a linear polarizer for passing components having a particular linear polarization and blocking components that do not have the particular polarization; and d. means for determining the concentration of water vapor in the sample based on a change in intensity of the light including the set of downshifted components supplied to the sample.

* * * * *